US00PP23256P2

(12) United States Plant Patent
Nelson et al.

(10) Patent No.: US PP23,256 P2
(45) Date of Patent: Dec. 18, 2012

(54) STRAWBERRY PLANT NAMED 'BG-3.324'

(50) Latin Name: *Fragaria ananassa*
Varietal Denomination: BG-3.324

(75) Inventors: Steven D. Nelson, Watsonville, CA (US); Michael D. Nelson, Watsonville, CA (US); Leo W. Stoeckle, Ventura, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 13/137,318

(22) Filed: Aug. 5, 2011

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'BG-3.324'. This new strawberry plant named 'BG-3.324' is primarily adapted to the growing conditions of the central coast of California, and is primarily characterized by its early fruit production, moderate to strongly expressed core cavity, medium to light yellow green foliage, orange red to red fruit color, and very large fruit size.

4 Drawing Sheets

Latin name of the genus and species of the plant claimed: *Fragaria ananassa.*

Variety denomination: 'BG-3.324'.

BACKGROUND OF THE INVENTION

The present invention relates to a new and distinct strawberry variety named 'BG-3.324'. This new variety is a result of a controlled cross made in 2003 in an ongoing breeding program between strawberry variety designated 'BG-1257' (a non-patented selection) and strawberry variety designated 'BG-1975' (patented, U.S. Plant Pat. No. 17,725). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the winter of 2005. After its selection, the new variety was asexually propagated by stolons in both San Joaquin County, Calif. and Siskiyou County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'BG-3.324' is primarily adapted to the climate and growing conditions of the central coast of California. The nearby Pacific Ocean provides the needed humidity and moderate temperatures to produce a strong vigorous plant and maintain fruit quality during the winter and spring production months.

The following traits have been repeatedly observed and are determined to be unique characteristics of 'BG-3.324', which in combination distinguish this strawberry plant as a new and distinct variety:

1. Early fruit production;
2. Moderate to strongly expressed core cavity;

3. Medium to light yellow green foliage;
4. Orange red to red fruit color; and
5. Very large fruit size.

The strawberry variety that is believed to be most closely related to the new variety 'BG-3.324' is 'BG-1975' (patented, U.S. Plant Pat. No. 17,725). In side-by-side comparisons to the similar strawberry variety 'BG-1975', 'BG-3.324' differs by the following combination of characteristics as described in Table 1.

TABLE 1

COMPARISON TO THE SIMILAR VARIETY

| Characteristic | 'BG-3.324' | 'BG-1975' (U.S. Plant Pat. No. 17,725) |
|---|---|---|
| Marketable yield (gm/plant) | 1,149 | 1,080 |
| Fruit predominant shape | Conical | Ranges from conical to almost cylindrical |
| Fruit size | Very large | Ranges from medium to large |
| 50% of plants with ripe fruit | Ranges from early to very early | Ranges from medium to early |
| Plant size | Medium | Ranges from medium to large |
| Expression of hollow center | Ranges from moderate to strong | Moderate |
| Shape of the base of the terminal leaflet | Obtuse | Acute |
| Fruiting truss anthocyanin intensity | Medium | Weak |
| Fruiting truss pubescence | Medium | Strong |

For identification, a series of molecular markers have been determined for this new variety.

'BG-3.324' differs from its parents, 'BG-1257' and 'BG-1975' by the following combination of characteristics as described in Table 2.

TABLE 2

COMPARISON WITH PARENT VARIETIES

| Characteristic | 'BG-3.324' | 'BG-633' (U.S. Plant Pat. No. 13,320) | 'BG-1445' |
|---|---|---|---|
| Marketable yield (gm/plant) | 1,149 | 628 | 1,080 |
| Fruit size | Very large | Ranges from medium to large | Ranges from medium to large |
| Plant size | Medium | Medium | Ranges from medium to large |
| Fruit color | Ranges from orange red to red | Red | Ranges from orange red to red |

BRIEF DESCRIPTIONS OF THE PHOTOGRAPHS

The accompanying color photographs illustrate the overall appearance of typical specimens of the new strawberry variety 'BG-3.324', at various stages of development as true as it is reasonably possible with color reproductions of this type. Color in the photographs may differ slightly from the color value cited in the botanical descriptions which accurately describe the color of 'BG-3.324'. The depicted plant and plant parts of the new strawberry variety 'BG-3.324' are approximately six months old. The photographs were taken in Ventura County, Calif.:

DETAILED BOTANICAL DESCRIPTION

Figure 1:
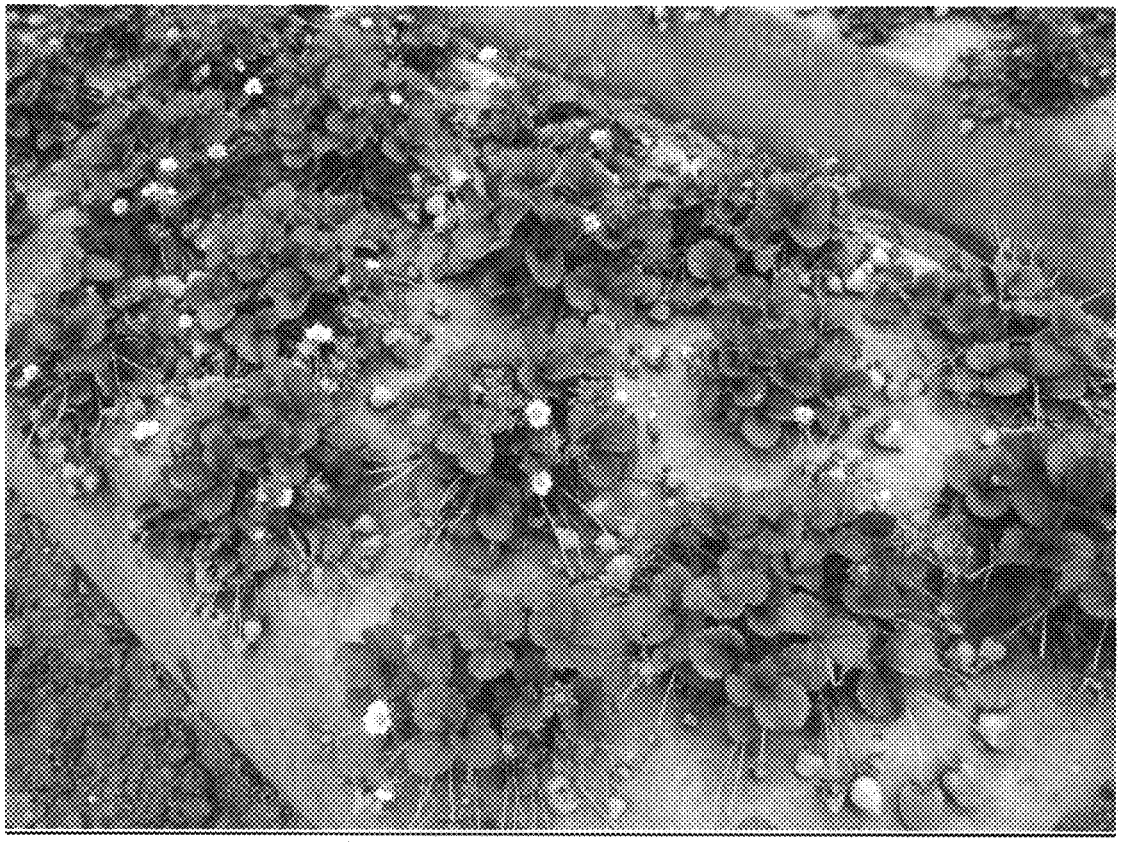
FIG. 1 shows typical fruiting field characteristics of 'BG-3.324', taken in the month of April 2011.
Figure 2:
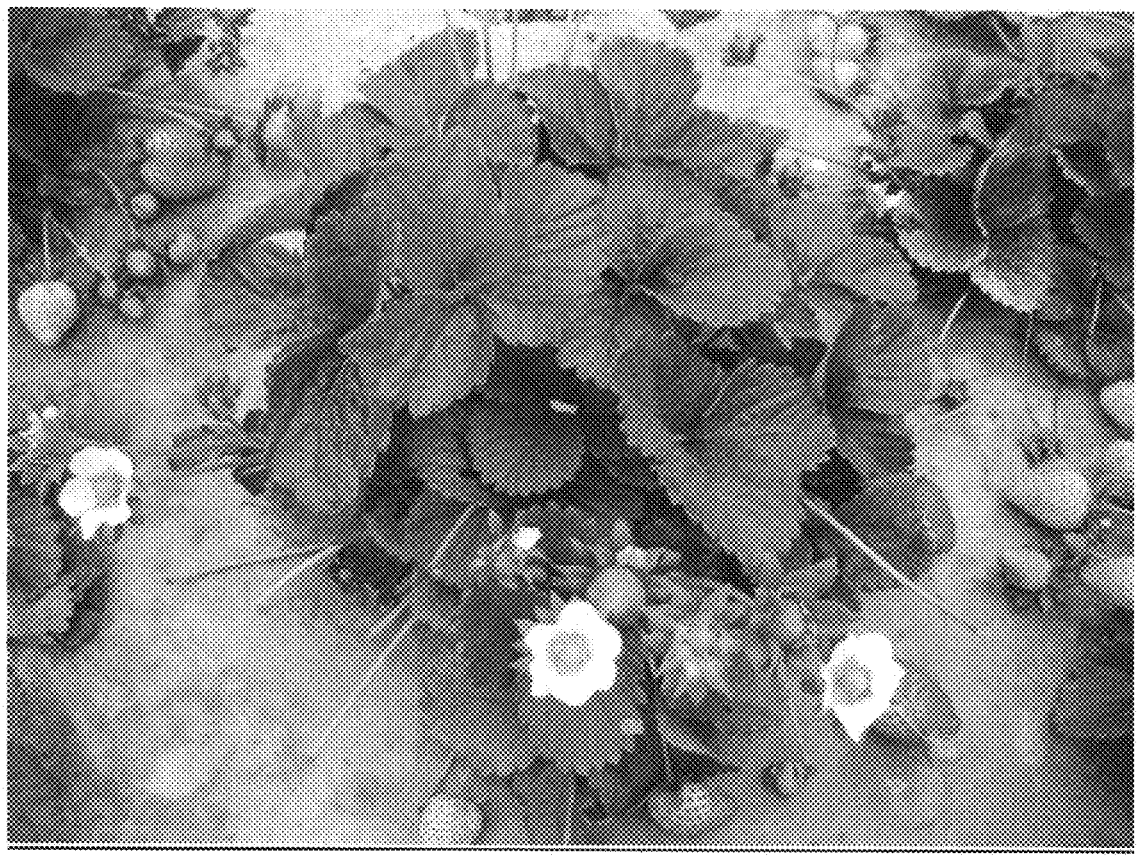
FIG. 2 shows a close-up view of the typical leaf structure of 'BG-3.324', taken in the month of April 2011.
Figure 3:
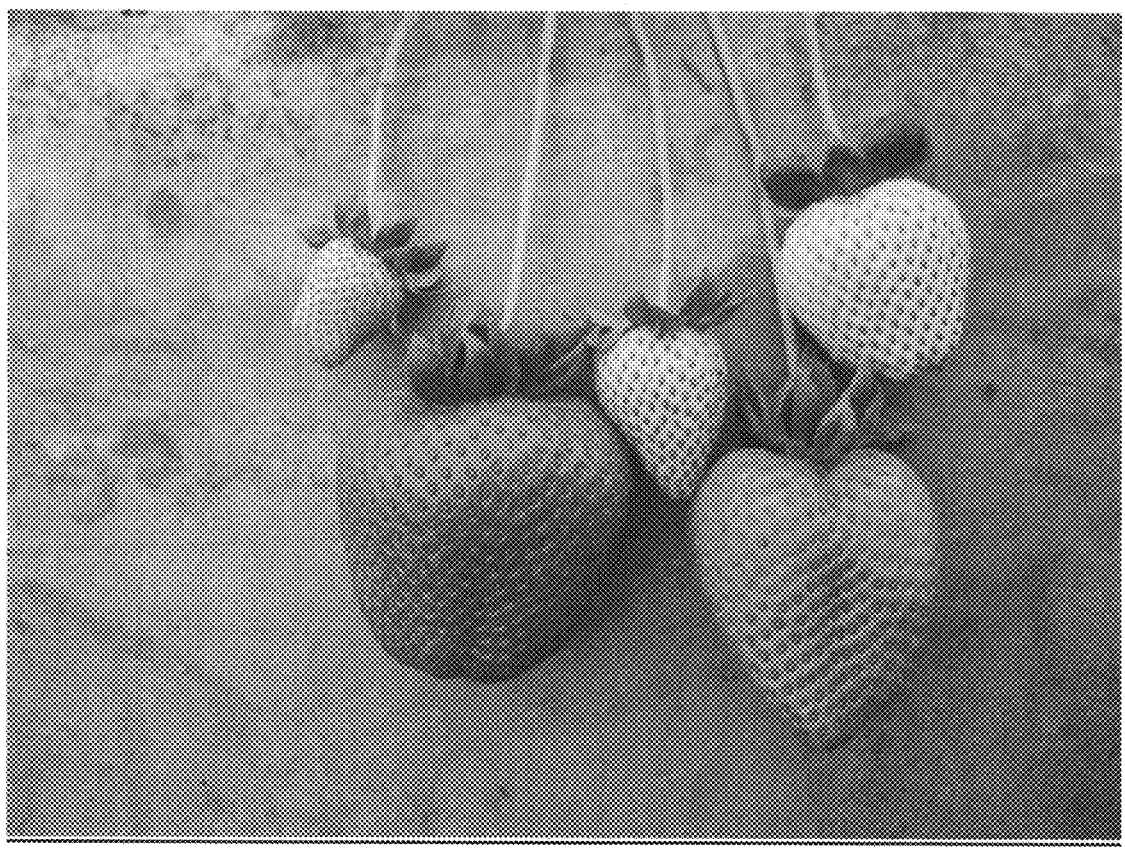
FIG. 3 shows typical mature and immature field fruit of 'BG-3.324', taken in the month of April 2011.
Figure 4:
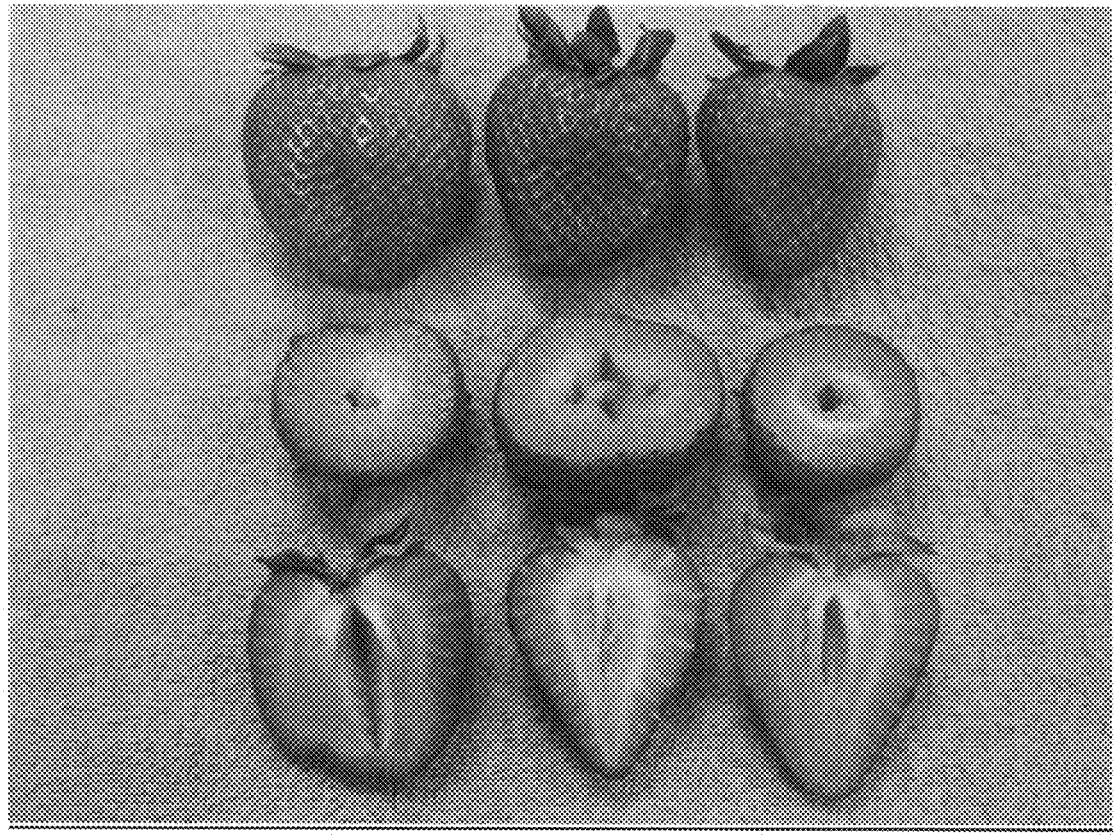
FIG. 4 shows typical internal and external mature fruit characteristics of 'BG-3.324', taken in the month of April 2011.

The new variety 'BG-3.324' has not been observed under all possible environmental conditions. The characteristics of the new variety 'BG-3.324' may vary in detail, depending upon variations in environmental factors, including weather (temperature, humidity and light intensity), day length, soil type and location. In addition, the characteristics of any parental variety or comparison variety included in Tables 1-9 of the present invention may vary in detail, depending upon variations in environmental factors, including weather (temperature, humidity and light intensity), day length, soil type and location.

The aforementioned photographs, together with the following description of the new variety 'BG-3.324', unless otherwise noted, are based on observations taken during the 2011 growing season in Ventura County, Calif. These measurements and ratings were taken from plants of 'BG-3.324' dug from a high-elevation nursery located in Siskiyou County, Calif. during early October 2010 and planted approximately four to five days later in Ventura County, Calif. The approximate age of the observed plants is six months. Yield observations and fruit quality characteristics are averaged from five years of data collected from the 2007 through 2011 growing seasons. Flower measurements and characteristics are from secondary flowers unless otherwise noted. Fruit characteristics and measurements are from secondary fruit unless otherwise noted.

Color terminology where noted follows The Royal Horticultural Society Colour Chart, London (2007).

The following tables 3-9 describe fruit, plant, stolon, foliage, fruiting truss, flower and pest disease characteristics of the new strawberry 'BG-3.324' in comparison to the similar strawberry variety 'BG-1975'.

TABLE 3

FRUIT CHARACTERISTICS

| Characteristic | 'BG-3.324' | 'BG-1975' (U.S. Plant Pat. No. 17,725) |
|---|---|---|
| Color of mature fruit | RHS 45B<br>Ranges from orange red to red | RHS 45A<br>Ranges from orange red to red |
| Color of internal flesh | RHS 45A<br>Dark red | RHS 44A<br>Medium red |
| Fruit length (cm) | 4.7 | 4.5 |
| Fruit width (cm) | 4.0 | 3.9 |
| Fruit length/width ratio | 1.20<br>Ranges from slightly longer than broad to much longer than broad | 1.14<br>Slightly longer than broad |
| Calyx diameter (cm) | 4.3 | 5.2 |
| Average fruit weight (gm) | 28.5 | 26.6 |
| Achene color, shaded side | RHS 153B<br>Yellow green group | RHS 152D<br>Yellow green group |
| Achene color, sun-exposed side | RHS 184A<br>Greyed purple group | RHS 183A<br>Greyed purple group |
| Achenes per berry | 364 | 300 |
| Achene weight (mg) | 0.60 | 0.67 |
| Marketable fruit yield (gm/plant) | 1,149 | 1,080 |
| Fruit size | Very large | Ranges from medium to large |
| Predominant fruit shape | Conical | Ranges from conical to almost cylindrical |
| Difference in shapes between primary and secondary fruit | Moderate | Ranges from slight to moderate |
| Band without achenes | Absent or very narrow | Absent or very narrow |
| Unevenness of fruit surface | Ranges from weak to medium | Weak |
| Evenness of fruit color | Ranges from slightly uneven to even | Ranges from slightly uneven to even |
| Fruit glossiness | Medium | Ranges from medium to strong |
| Insertion of achenes | Ranges from below surface to level with surface | Ranges from below surface to level with surface |
| Insertion of calyx | In basin | In basin |
| Attitude of calyx | Ranges from collapsing to spreading | Spreading |
| Size of calyx in relation to fruit diameter | Ranges from slightly smaller to same size | Ranges from slightly larger to much larger |
| Adherence of calyx | Strong | Very strong |
| Firmness of fruit skin | Medium | Ranges from medium to strong |
| Firmness of fruit flesh | Firm | Medium |
| Keeping quality | Ranges from good to moderate | Good |
| Distribution of red color of the flesh | Marginal and central | Marginal and central |
| Hollow center expression | Ranges from moderate to strong | Moderate |
| Fruit flavor | Good | Very good |

TABLE 3-continued

| FRUIT CHARACTERISTICS | | |
|---|---|---|
| Characteristic | 'BG-3.324' | 'BG-1975' (U.S. Plant Pat. No. 17,725) |
| Soluble solids (% brix) | 8.4 | 8.6 |
| Time of first flowering | Ranges from very early to early | Ranges from early to medium |
| Time of first harvesting | Ranges from very early to early | Ranges from early to medium |
| Harvest period | Late December to mid May | Early January to late May |
| Type of bearing | Not remontant | Not remontant |

TABLE 4

| PLANT CHARACTERISTICS | | |
|---|---|---|
| Characteristic | 'BG-3.324' | 'BG-1975' (U.S. Plant Pat. No. 17,725) |
| Plant height (cm) | 19.0 | 23.0 |
| Plant spread (cm) | 25.5 | 26.1 |
| Plant size | Medium | Ranges from large to medium |
| Plant habit | Globose | Globose |
| Plant density | Medium | Medium |
| Plant vigor | Medium | Ranges from medium to strong |

TABLE 5

| STOLON CHARACTERISTICS | | |
|---|---|---|
| Characteristic | 'BG-3.324' | 'BG-1975' (U.S. Plant Pat. No. 17,725) |
| Stolon color | RHS 146C Yellow green group | RHS 146D Yellow green group |
| Stolon anthocyanin coloration | RHS 181A Greyed red group | RHS 182A Greyed red group |
| Stolon anthocyanin intensity | Strong | Weak |
| Average stolon quantity | Ranges from medium to many | Medium |
| Stolon diameter at bract (mm) | 3.4 | 3.1 |
| Stolon pubescence | Medium | Strong |
| Attitude of hairs | Upwards | Slightly outward |

TABLE 6

| FOLIAGE CHARACTERISTICS | | |
|---|---|---|
| Characteristic | 'BG-3.324' | 'BG-1975' (U.S. Plant Pat. No. 17,725) |
| Foliage: | | |
| Color of upper surface | RHS 146B Ranges from light yellow green to medium yellow green | RHS 146B Ranges from light yellow green to medium yellow green |
| Color of underside | RHS 147C Yellow green group | RHS 147C Yellow green group |
| Shape in cross section | Slightly concave to flat | Slightly concave to flat |
| Interveinal blistering | Medium | Ranges from weak to medium |
| Leaf glossiness | Medium | Ranges from weak to medium |
| Number of leaflets | 3 | 3 |

TABLE 6-continued

| FOLIAGE CHARACTERISTICS | | |
|---|---|---|
| Characteristic | 'BG-3.324' | 'BG-1975' (U.S. Plant Pat. No. 17,725) |
| Terminal Leaflet: | | |
| Length (cm) | 6.9 | 7.0 |
| Width (cm) | 6.3 | 6.2 |
| Length/width ratio | 1.09 | 1.13 |
| | Ranges from as long as broad to longer than broad | Ranges from as long as broad to longer than broad |
| Serrations/leaf | 16.8 | 20.8 |
| Leaf Size | Ranges from medium to small | Ranges from medium to small |
| Shape of base | Obtuse | Acute |
| Shape of teeth | Rounded | Rounded |
| Petiole: | | |
| Petiole color | RHS 144B Yellow green group | RHS 144B Yellow green group |
| Petiole length (cm) | 14.0 | 15.5 |
| Petiole diameter (mm) | 3.2 | 3.7 |
| Petiolule color | RHS 144B Yellow green group | RHS 144B Yellow green group |
| Petiolule length (mm) | 7.6 | 11.7 |
| Petiole pubescence | Heavy | Heavy |
| Attitude of hairs | Strongly outward | Strongly outward |
| Stipule: | | |
| Color | RHS 146A Yellow green group | RHS 146C Yellow green group |
| Anthocyanin coloration | RHS 58A Red purple group | RHS 61B Red purple group |
| Anthocyanin intensity | Weak | Weak |
| Length (mm) | 13.0 | 16.0 |
| Width (mm) | 10.3 | 10.1 |

TABLE 7

| FRUITING TRUSS CHARACTERISTICS | | |
|---|---|---|
| Characteristic | 'BG-3.324' | 'BG-1975' (U.S. Plant Pat. No. 17,725) |
| Anthocyanin coloration | RHS 181C Greyed red group | RHS 181C Greyed red group |
| Anthocyanin intensity | Medium | Weak |
| Length at maturity (cm) | 26.4 | 28.6 |
| Position relative to foliage | Ranges from level with to above the foliage | Ranges from level with to above the foliage |
| Pubescence | Medium | Strong |
| Attitude at first pick | Prostrate | Prostrate |

TABLE 8

| FLOWER CHARACTERISTICS | | |
|---|---|---|
| Characteristic | 'BG-3.324' | 'BG-1975' (U.S. Plant Pat. No. 17,725) |
| Petal color | RHS NN155C White group | RHS NN155C White group |
| Sepal color | RHS 137B Green group | RHS 138A Green group |
| Corolla diameter (mm) | 29.8 | 27.7 |
| Calyx diameter (mm) | 34.6 | 38.8 |
| Petal length (mm) | 11.0 | 10.7 |
| Petal width (mm) | 11.6 | 10.5 |
| Petal length/width ratio | .95 | 1.02 |

TABLE 8-continued

FLOWER CHARACTERISTICS

| Characteristic | 'BG-3.324' | 'BG-1975' (U.S. Plant Pat. No. 17,725) |
|---|---|---|
| Petals/flower | 6.4 | 6.3 |
| Sepal length (mm) | 13.5 | 15.5 |
| Sepal width (mm) | 5.5 | 5.5 |
| Sepal length/width ratio | 2.43 | 2.81 |
| Sepals/flower | 12.4 | 12.6 |
| Size of calyx relative to corolla | Larger | Larger |
| Size of inner calyx relative to outer calyx | Ranges from smaller to same | Ranges from smaller to same |
| Relative position of petals | Overlapping | Overlapping |

TABLE 9

PEST AND DISEASE REACTIONS

| Characteristic | 'BG-3.324' | 'BG-1975' (U.S. Plant Pat. No. 17,725) |
|---|---|---|
| Two-spotted spider mite | Moderately susceptible | Moderately susceptible |
| Powdery mildew | Moderately susceptible | Moderately susceptible |
| Botrytis fruit rot | Moderately susceptible | Moderately susceptible |
| Angular leaf spot | Susceptible | Susceptible |

We claim:

1. A new and distinct strawberry plant named 'BG-3.324', as herein described and illustrated by the characteristics set forth above.

* * * * *